US009867398B2

(12) United States Patent
Guo et al.

(10) Patent No.: US 9,867,398 B2
(45) Date of Patent: Jan. 16, 2018

(54) ULTRASONIC E-CIGARETTE DEVICE

(71) Applicants: David Guo, Irvine, CA (US); Hong Xi Guo, Rancho Cucamonga, CA (US)

(72) Inventors: David Guo, Irvine, CA (US); Hong Xi Guo, Rancho Cucamonga, CA (US)

( * ) Notice: Subject to any disclaimer, the term of this patent is extended or adjusted under 35 U.S.C. 154(b) by 88 days.

(21) Appl. No.: 15/096,180

(22) Filed: Apr. 11, 2016

(65) Prior Publication Data

US 2016/0295913 A1 Oct. 13, 2016

Related U.S. Application Data

(60) Provisional application No. 62/145,384, filed on Apr. 9, 2015.

(51) Int. Cl.

| | |
|---|---|
| ***A61M 15/00*** | (2006.01) |
| ***A61M 11/00*** | (2006.01) |
| ***B05B 17/06*** | (2006.01) |
| ***B05B 17/00*** | (2006.01) |
| ***A24F 47/00*** | (2006.01) |

(52) U.S. Cl.
CPC ........ *A24F 47/002* (2013.01); *B05B 17/0615* (2013.01)

(58) Field of Classification Search
CPC ......................... A24F 47/008; B05B 17/0615; A61M 11/042; A61M 15/0066
See application file for complete search history.

(56) References Cited

U.S. PATENT DOCUMENTS 6,732,944 B2 * 5/2004 Litherland ........... A61M 11/005 239/102.1
8,864,046 B2 * 10/2014 Chen ....................... F04B 23/04 239/102.1
9,050,424 B2 * 6/2015 Van Der Mark .... A61M 11/005
9,126,218 B2 * 9/2015 Sasaki ................. B05B 17/0646
9,333,523 B2 * 5/2016 Lowy .................. B05B 17/0646
9,352,108 B1 * 5/2016 Reed ................. A61M 15/0091

* cited by examiner

*Primary Examiner* — Xuong Chung Trans
(74) *Attorney, Agent, or Firm* — K&L Gates LLP; Jordan A. Kwan

(57) ABSTRACT

Systems, methods, and apparatuses are presented for an e-cigarette device that atomizes the liquid through ultrasonic vibrations, thereby generating micro-droplets that can be absorbed through breathing, similar to breathing in a mist or vapor. No heating elements are involved, thereby leading to no burnt elements and reducing second-hand smoke effects.

20 Claims, 16 Drawing Sheets

100

100

Components 3-6 Assembled

Dimensions

ULTRASONIC E-CIGARETTE DEVICE

CROSS REFERENCE TO RELATED APPLICATION

This application claims the benefit of U.S. Provisional Application 62/145,384, filed Apr. 9, 2015, and titled, "ULTRASONIC E-CIGARETTE DEVICE," the disclosure of which is incorporated herein by reference in its entirety and for all purposes.

BACKGROUND

Conventional e-cigarette devices tend to rely on inducing high temperatures of a metal component configured to heat a liquid in the e-cigarette, thus vaporizing the liquid that can be breathed in. Problems with conventional e-cigarettes may include the possibility of burning metal and subsequent breathing in of the metal along with the burnt liquid. In addition, some may not prefer the burnt smell caused by the heated liquid. In addition, a conventional e-cigarette may be designed to create a substantial amount of smoke, simulated by the burnt liquid, that can be akin to second-hand smoke. It is desirable to develop devices that minimize or eliminate at least some of these problems.

BRIEF SUMMARY

Systems and apparatuses are presented for devices configured to atomize liquid into a breathable vapor. In some embodiments, an apparatus for atomizing liquid into a breathable vapor comprises: a liquid container housing comprising an inside volume and a bottom surface; an inner liquid container housing positioned inside the liquid container such that liquid is configured to flow in between the inside volume of the liquid container housing and an outside volume of the inner liquid container housing, within a gap formed at a bottom end of the liquid container, and into an inside volume of the inner liquid container housing through the gap at the bottom end of the liquid container; and an ultrasonic liquid atomizer component positioned inside the inner liquid container. The ultrasonic liquid atomizer may include: an inner disk housing comprising a water channel and a liquid opening fluidically coupled to the water channel; a first ultrasonic sprayer disk fluidically coupled to the liquid opening of the inner disk housing on a first side; a second ultrasonic sprayer disk fluidically coupled to the liquid opening of the inner disk housing on a second side opposite the first side; a first outer disk housing enclosing the first ultrasonic sprayer disk between the inner disk housing and the first outer disk housing and comprising a first air channel fluidically coupled to the first ultrasonic sprayer disk; and a second outer disk housing enclosing the second ultrasonic sprayer disk between the inner disk housing and the second outer disk housing and comprising a second air channel fluidically coupled to the second ultrasonic sprayer disk. The ultrasonic liquid atomizer may be configured to vaporize liquid flowing within the inner liquid container directionally out through the first air channel and the second air channel by ultrasonically vibrating the first and second ultrasonic sprayer disks upon contact with the liquid.

In some embodiments of the apparatus, the inner liquid container further comprises a third air channel positioned within the inside volume of the inner liquid container and outside of the ultrasonic liquid atomizer; wherein the third air channel is fluidically coupled to at least one of the first and second air channels and is physically isolated from the gap at the bottom of the liquid container by the positioning of the ultrasonic liquid atomizer.

In some embodiments, the apparatus may include a cap enclosing the liquid container at a top end and encapsulating the inner liquid container and the ultrasonic liquid atomizer within the liquid container.

In some embodiments of the apparatus, the cap comprises an airway fluidically coupled to the third air channel of the inner liquid container configured to allow liquid vapor to flow out of the cap.

In some embodiments of the apparatus, the cap further comprises a mouthpiece fluidically coupled to the airway and configured to allow suction of liquid vapor flowing out of the airway.

In some embodiments, the apparatus further comprises an integrated circuit coupled to the bottom end of the liquid container and communicatively coupled to the ultrasonic liquid atomizer, the integrated circuit configured to cause the first and second ultrasonic sprayer disks to vibrate.

In some embodiments, the apparatus further comprises a battery tube configured to contain a battery and encasing at least a portion of the integrated circuit.

In some embodiments of the apparatus: the third air channel of the inner liquid container is fluidically coupled to the first air channel and not the second air channel; the inner liquid container further comprises a fourth air channel positioned within the inside volume of the inner liquid container and outside of the ultrasonic liquid atomizer; and the fourth air channel is fluidically coupled to the second air channel and is physically isolated from the gap at the bottom of the liquid container by the positioning of the ultrasonic liquid atomizer.

In some embodiments, the apparatus further comprises a cap enclosing the liquid container at a top end and encapsulating the inner liquid container and the ultrasonic liquid atomizer within the liquid container. The cap may include: a first airway fluidically coupled to the third air channel of the inner liquid container and configured to allow liquid vapor to flow out of the cap; and a second airway fluidically coupled to the fourth air channel of the inner liquid container and configured to allow liquid vapor to flow out of the cap.

In some embodiments of the apparatus, the ultrasonic liquid atomizer further comprises: third and fourth ultrasonic sprayer disks fluidically coupled to the liquid opening of the inner disk housing on the first side; and fifth and sixth ultrasonic sprayer disks fluidically coupled to the liquid opening of the inner disk housing on the second side.

In some embodiments of the apparatus, the first outer disk housing further encloses the third and fourth ultrasonic sprayer disks between the inner disk housing and the first outer disk housing and further comprises: a third air channel fluidically coupled to the third ultrasonic sprayer disk; and a fourth air channel fluidically coupled to the fourth ultrasonic sprayer disk; and the second outer disk housing further encloses the fifth and sixth ultrasonic sprayer disks between the inner disk housing and the second outer disk housing and further comprises: a fifth air channel fluidically coupled to the fifth ultrasonic sprayer disk; and a sixth air channel fluidically coupled to the sixth ultrasonic sprayer disk.

In some embodiments, an alternative apparatus for atomizing liquid into a breathable vapor is presented. The alternative apparatus may include: a liquid container housing comprising an inside volume, a bottom surface; and a hinge positioned on a top surface opposite the bottom surface and above the inside volume; an ultrasonic liquid atomizer component positioned on the top surface and above the inside volume and rotatably coupled to the hinge. The ultrasonic liquid atomizer may include: an ultrasonic sprayer disk; a spray disk housing; a bottom plate housing comprising a liquid channel opening; and a top plate housing comprising an air channel opening. Wherein: the ultrasonic sprayer disk is encapsulated within an enclosure formed by coupling of the spray disk housing inbetween the bottom plate housing and the top plate housing; the ultrasonic sprayer disk is fluidically coupled to the liquid channel opening of the bottom plate housing and the air channel opening of the top plate housing; and the ultrasonic liquid atomizer is configured to vaporize liquid flowing within the inside volume directionally out through the liquid channel opening and the air channel opening by ultrasonically vibrating the ultrasonic sprayer disk upon contact with the liquid.

In some embodiments, the alternative apparatus further comprises a liquid stopper and a cap.

In some embodiments of the alternative apparatus, the cap encloses the top surface of the liquid container and the liquid stopper is positioned within the inside volume of the liquid container.

In some embodiments of the alternative apparatus, an airtight seal is formed within the inside volume inbetween the cap and the liquid stopper by the enclosing of the top surface by the cap and the liquid stopper.

In some embodiments of the alternative apparatus, when liquid stored in the inside volume inbetween the liquid stopper and the ultrasonic liquid atomizer is vaporized directionally out through the liquid air channel, the liquid stopper is configured to rise up toward the ultrasonic sprayer disk due to a vacuum caused by the vaporization of the liquid and the airtight seal.

In some embodiments, the alternative apparatus further comprises an integrated circuit coupled to the bottom end of the liquid container and communicatively coupled to the ultrasonic liquid atomizer, the integrated circuit configured to cause the ultrasonic sprayer disk to vibrate.

In some embodiments, the alternative apparatus further comprises a battery tube configured to contain a battery and encasing at least a portion of the integrated circuit.

In some embodiments, the alternative apparatus further comprises a cap comprising an airway fluidically coupled to the air channel opening of the ultrasonic liquid atomizer and configured to allow liquid vapor to flow out of the cap.

In some embodiments of the alternative apparatus, the cap further comprises a mouthpiece fluidically coupled to the airway and configured to allow suction of liquid vapor flowing out of the airway.

BRIEF DESCRIPTION OF THE DRAWINGS

Some embodiments are illustrated by way of example and not limitation in the figures of the accompanying drawings.

DETAILED DESCRIPTION

Figure 1A:
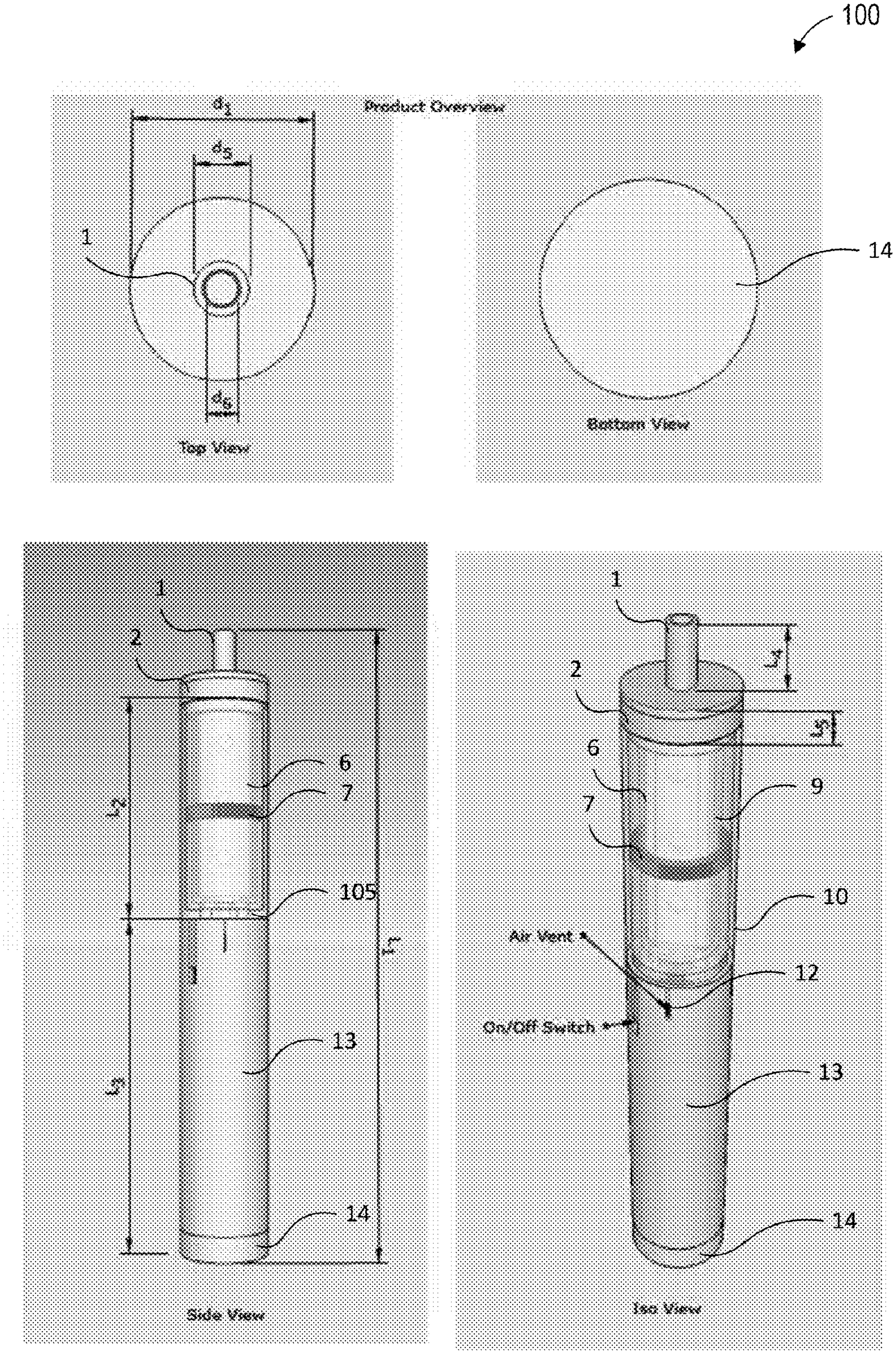
FIG. 1A shows various angles of an ultrasonic e-cigarette device, according to some embodiments.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used in this specification and the appended claims, the singular forms "a," "an," and "the" include plural referents unless the context clearly indicates otherwise.

Conventional e-cigarette devices tend to rely on inducing high temperatures of a metal component configured to heat a liquid in the e-cigarette, thus vaporizing the liquid that can be breathed in. The liquid typically contains nicotine and flavorings blended into a solution of 50% propylene glycol (PG) and 50% vegetable glycerin (VG), which is vaporized through an atomizer (resister) at about 200 degrees Celsius. Problems with conventional e-cigarettes may include the possibility of burning metal and subsequent breathing in of the metal along with the burnt liquid. In addition, some may not prefer the burnt smell caused by the heated liquid. In addition, a conventional e-cigarette may be designed to create a substantial amount of smoke, simulated by the burnt liquid, that can be akin to second-hand smoke.

In contrast, aspects of the present disclosure include an e-cigarette device that atomizes the liquid through ultrasonic vibrations, which produces micro water bubbles in the liquid. When the bubbles come into contact with random air molecules of high temperature, water droplets of about 2-5 microns vaporize into the air, thereby generating micro-droplets that can be absorbed through breathing, similar to breathing in a mist or vapor. For example, the ultrasonic e-cigarette of the present disclosures may produce a cool mist that contains more than 80% of H2O mixed with nicotine and other ingredients including but not limited to PG, VG, flavorings, and natural oils. In some embodiments, the nicotine mixture is less than 2% or more than 20% by volume. No heating elements are involved, thereby leading to no burnt elements and reducing second-hand smoke effects. As used herein, descriptions of "water" may refer to a liquid combination of $H_2O$ and other ingredients conventionally used in e-cigarette devices utilizing liquid mixtures.

The ultrasonic device according to the present disclosures will contact the liquid on one surface and spray it out the other surface, bursting outwards a mist that is close to room temperature. As a result, there will be no burnt flavor of any kind for the user (as opposed to current products). This allows for aspects of the present disclosures to produce less smoke, making it possible to be used anywhere without disturbing other people.

In some embodiments, the e-cigarette device will channel the mist from 1 to 6 of these ultrasonic disks (may vary by product line and by manual or automatic setting adjustments) from one or more air channels, which are like semicircular straws enclosing the spraying side of the disks. On the opposite side of the disks, a thin water channel will be attached to them. In some embodiments, the e-cigarette device will have the water channel between or mounted on one side of the disks. The combination of the water channel (3), disks (5), and airway (6) & (8) is called the emission chamber. In some embodiments, this emission chamber is removable for ease of cleaning.

Surrounding the emission chamber or closely attached to it is a liquid container (9) & (10). The liquid container includes a movable liquid seal (7) that stays on the surface of the liquid. The seal tells the user the current liquid level remaining. The movable seal (7), together with the thin water channel (3) will ensure the liquid is continuously supplied to the disks (5) because atmospheric pressure will push down on the liquid seal (7). In some embodiments, a transparent liquid container (9) & (10) and a semi-transparent emission chamber are present so that the user can see the liquid level as well as the ultrasonic vaporization process.

In some embodiments, the airways (6) & (9) are connected to the upper portion of the battery tube (13) where the circuitry (11) is located. This will allow for automatic variable output of the spray disk because the circuitry will have a mechanical component that links to the flow of air.

In summary, the e-cigarette device of the present disclosures is a more powerful version of current portable medical nebulizers, in the shape and size of current e-cigarettes and with a particular structure for effective vaporization. It is a healthier alternative to cigarettes and current e-cigarettes products.

Figure 1B:
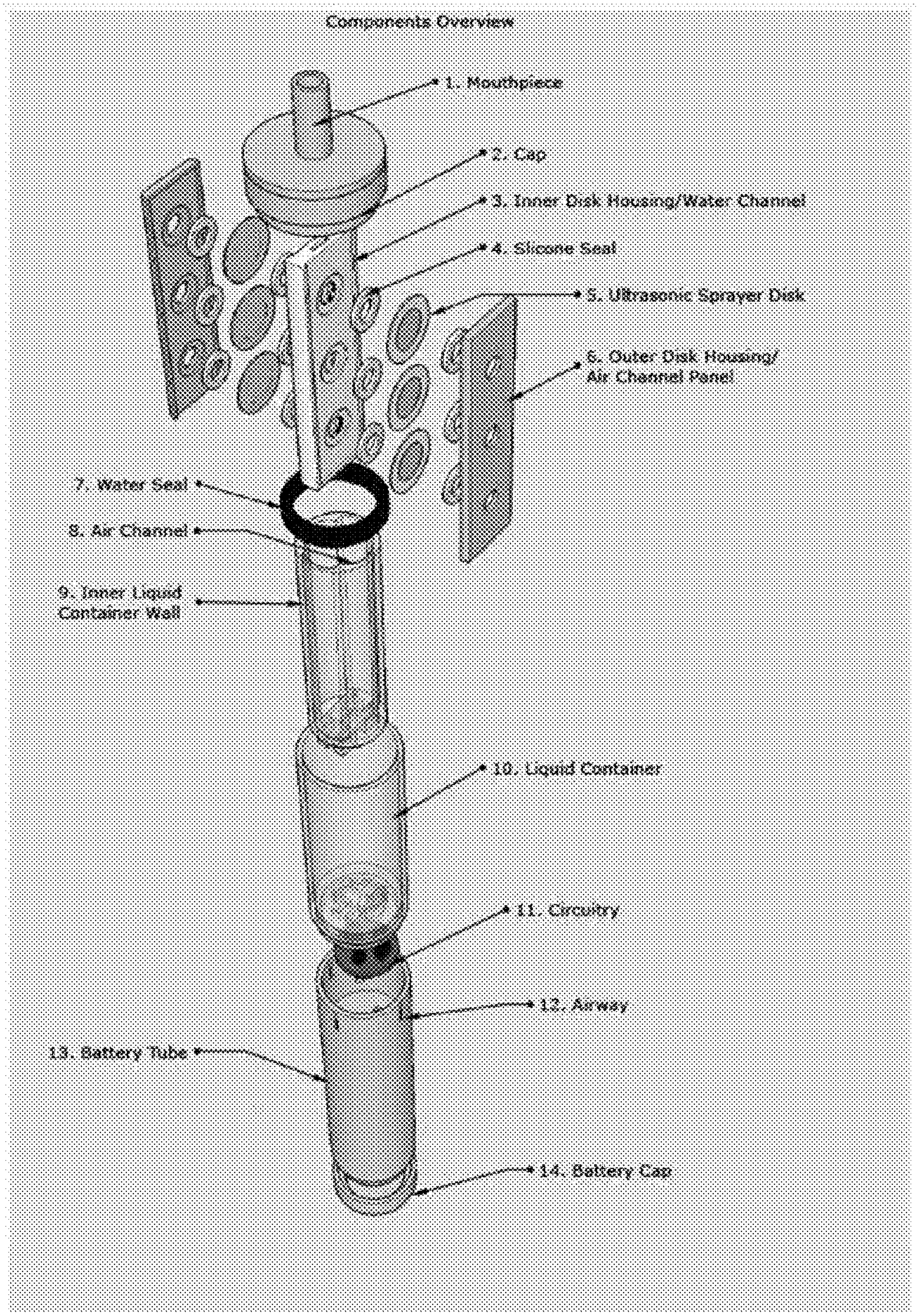
FIG. 1B is an exploded view of components of the ultrasonic e-cigarette device, according to some embodiments.

Referring to FIGS. 1A and 1B, illustrations 100 (FIG. 1A) and 150 (FIG. 1B) show various perspective views and an exploded view, respectively, of an ultrasonic e-cigarette device, according to some embodiments. Various components include a mouthpiece 1, a cap 2, an inner disk housing/water channel 3, one or more seals 4 (e.g., silicone seals), one or more ultrasonic sprayer disks 5, one or more outer disk housing/air channel panel 6, a water seal 7, the air channel 8, an inner liquid container wall 9, the outer liquid container 10, circuitry for actuating the ultrasonic disk system 11, an airway 12, a battery tube 13, and a battery cap 14. These example components will be described in more detail, below.

Cap and Mouthpiece (1) & (2)

Figure 2:
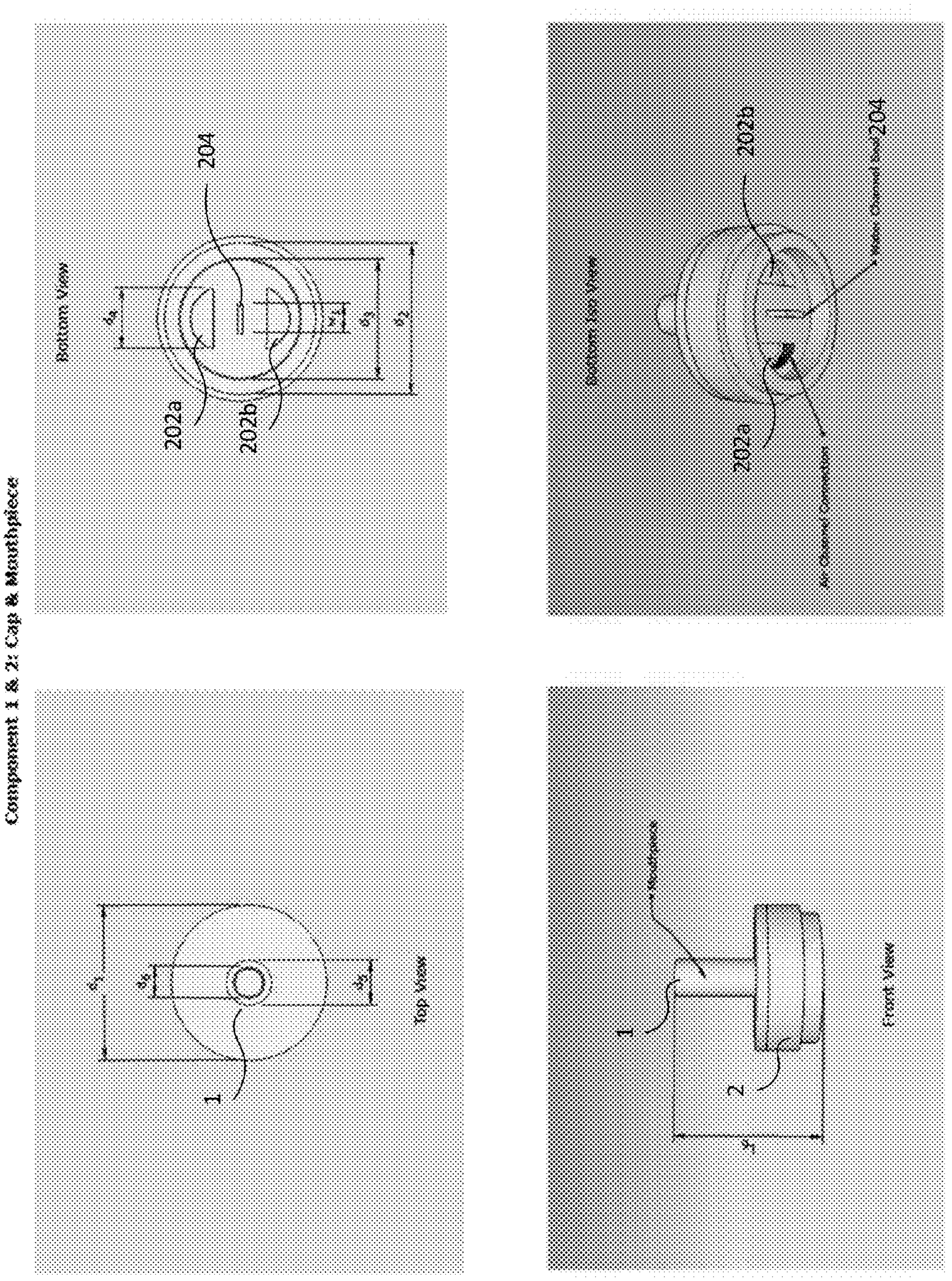
FIG. 2 shows diagrams of different views of example cap and mouthpiece components of the ultrasonic e-cigarette device, according to some embodiments.

Referring to FIG. 2, illustrations of the cap 2 and mouthpiece 1 components are shown. From the bottom view, one can clearly see the two, semicircular airway openings 202*a* and 202*b*, which connect to the air channels 8 of component 9 (see FIG. 1B). Also from the bottom view, the small rectangular tip 204 in the middle of the cap 2 is designed to seal off the water channel of the inner disk housing 3 so that no air passes through. With the cap off, liquid will be refilled through the top of this water channel of the inner disk housing 3 until the water seal 7 rises to the full level (see FIG. 1B).

Water Seal, Liquid Container and Water Channel (7), (9), (10), (3)

Figure 5:
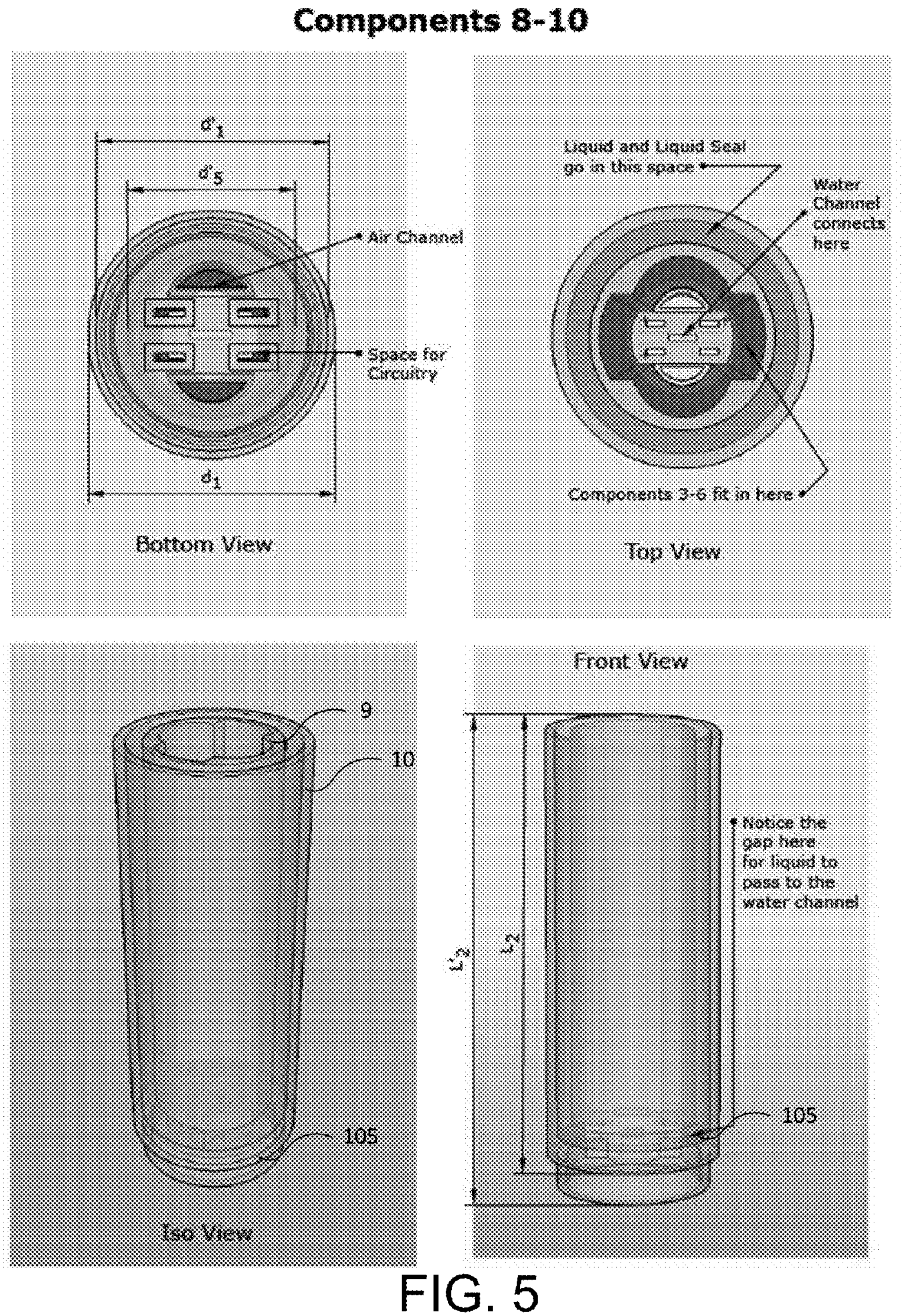
FIG. 5 shows various angles of the liquid container and outer container wall of the ultrasonic e-cigarette device, according to some embodiments.

Referring to FIGS. 1A and 5, most of the water-based liquid sits beneath the water seal 7, and between the outer liquid container tube 10 and the inner liquid container tube 9. Some, however, sits in the gap 105 (see FIG. 1A) at the bottom between 9 and 10 to allow water flow into the water channel of the inner disk housing 3. That is, water flows from the very bottom to near the top where the water is sealed off by the cap 2.

The system works by the physics of suction: as the ultrasonic spray disk 5 sprays the mist into the air channel between 6 and 8, it also uses up the water in the water channel flowing through the middle of 3. Provided that firstly there is no air or water leak between the seals 4, inner disk housing 3, and the spray disks 5, and secondly there is no air or water leak between the middle tip of the cap 2 covering the water channel in the middle of 3, conservation of mass requires the water to flow continuously from the water channel. This requires the liquid container combination of 9 & 10 to not be air sealed so that the atmospheric pressure will push the water seal 7 downward (hence the water) as the water is used up by the disks. This system works at all angles and orientation because the atmospheric pressure is strong enough to overcome the weight of the water in the container.

Emission Chamber: Inner Disk Housing and Outer Disk Housing (3) & (6)

Figure 3:
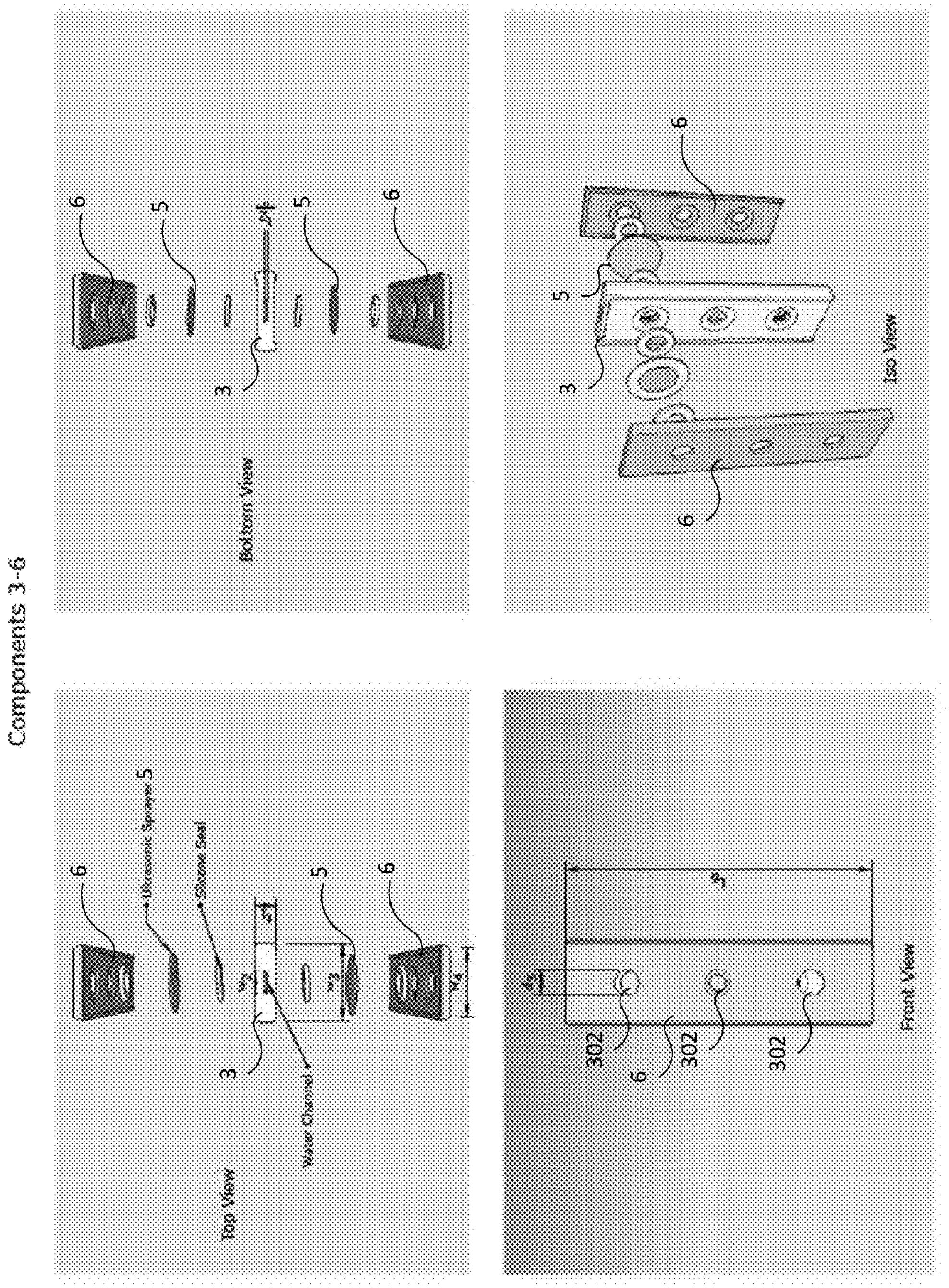
FIG. 3 shows exploded view diagrams of the emission chamber of the ultrasonic e-cigarette device, according to some embodiments.
Figure 4:
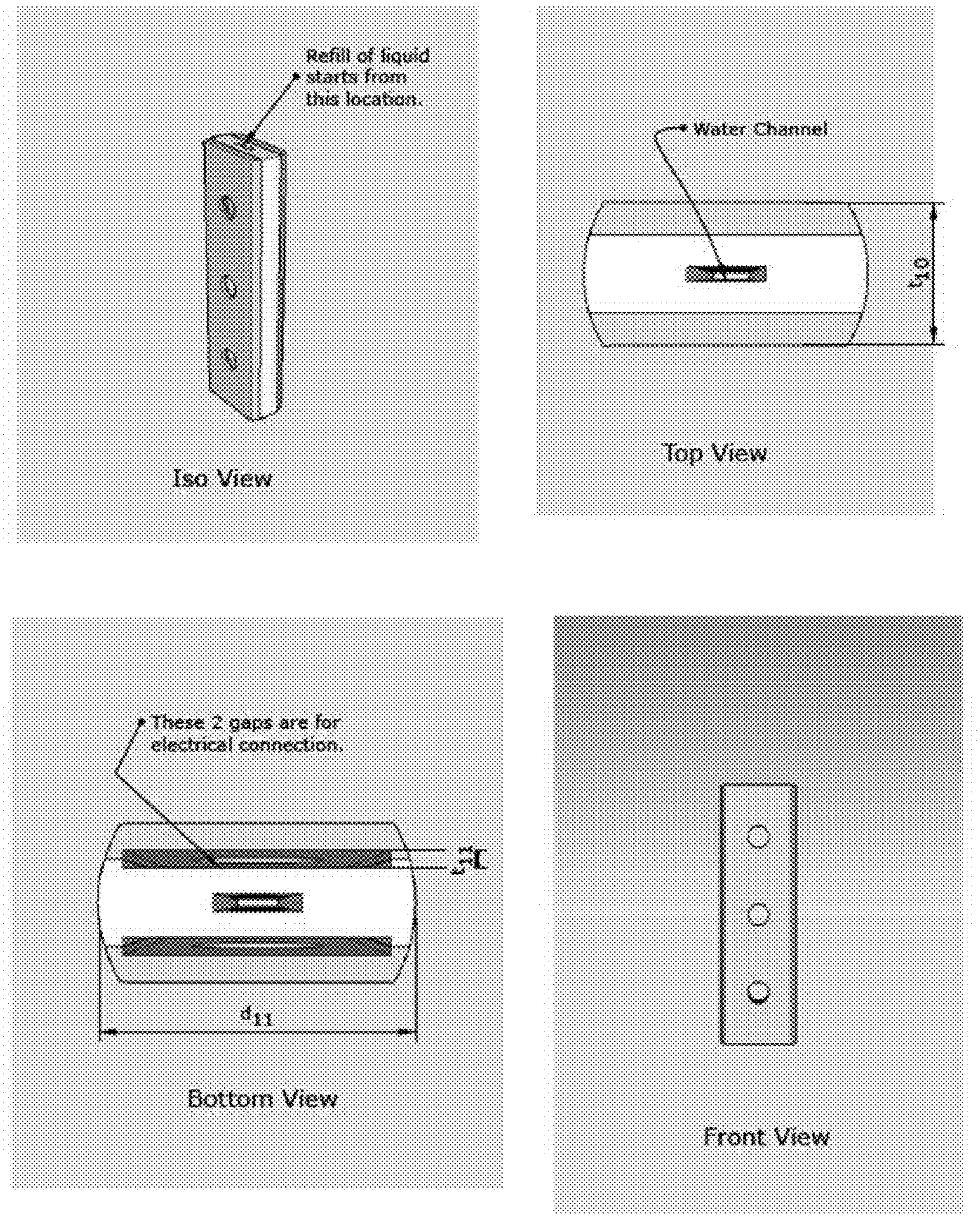
FIG. 4 shows various angles of the assembled emission chamber of the ultrasonic e-cigarette device, according to some embodiments.

Referring to FIGS. 3 and 4, the inner disk housing 3 contains the water channel, which has, in this example, three circular openings on each side to allow water to connect to the spray disk 5. The outer disk housing 6 encloses the spray disks 5 together with the inner disk housing 3. The outer disk housing 6 also contains three concentric circular openings 302 to allow the mist to pass through to the air channels 8.

In some embodiments, there is ~1 mm of space between 3 & 6 to allow placement of two seals sandwiching the spray disk 5 as well as electrical wiring or connection. Notice that the top of the disk housing combination 3 & 6 is sealed off while the bottom contains two openings to allow electrical connection with the circuitry 11 (see FIG. 1B).

Ultrasonic Sprayer Disk (5)

Referring to FIGS. 1, 3, and 4, the ultrasonic sprayer disks 5 contain tiny micro holes that are small enough to prevent water or other e-cigarette liquid from leaking through due to surface tension, but still allow for the liquid to be atomized and pass through the holes when the ultrasonic sprayer disks are vibrated. The ultrasonic disks 5 thus separate the liquid in the water channel from the air in the outer container.

Alternative Embodiments

Figure 6:
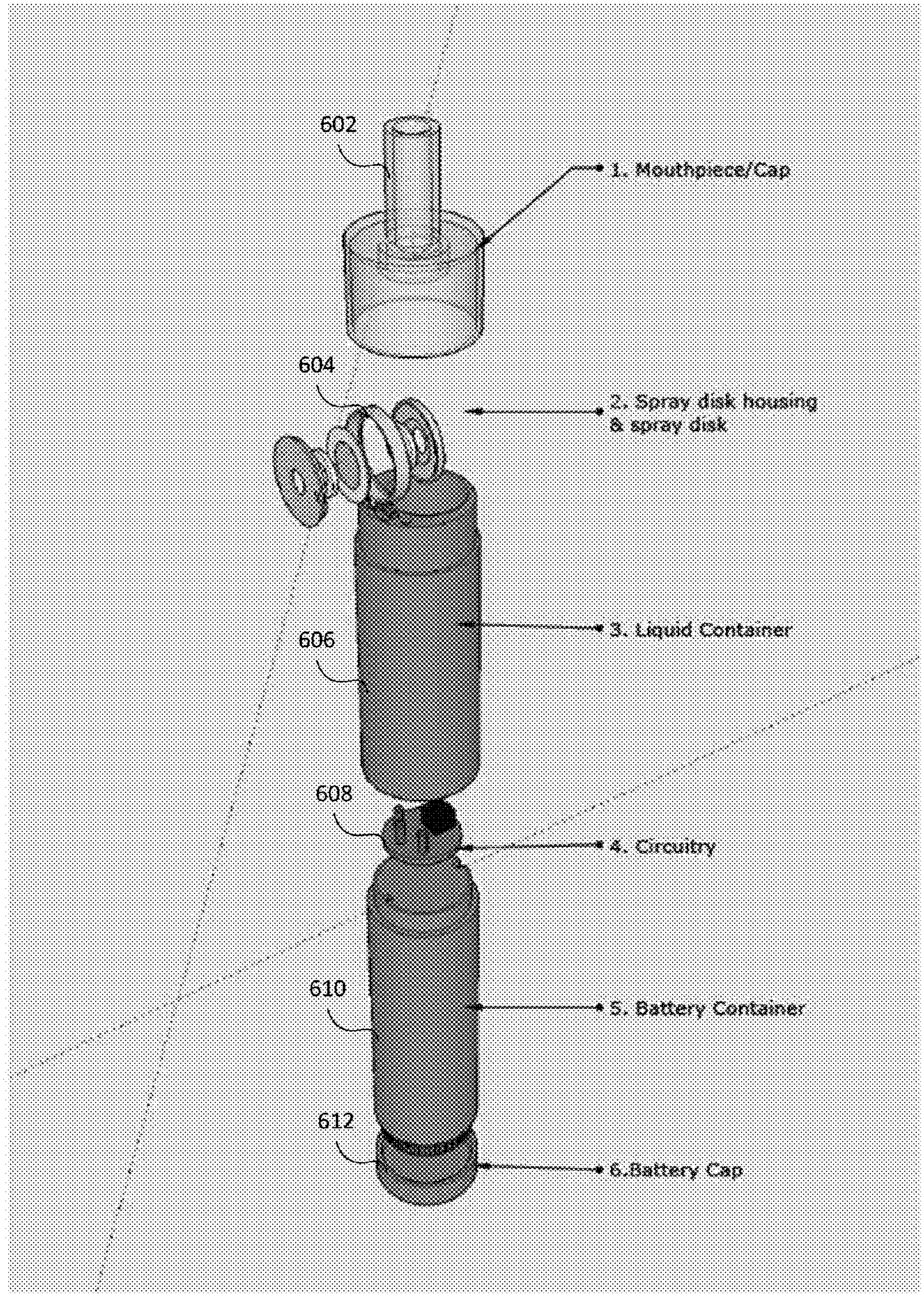
FIG. 6 shows an exploded view of an alternative implementation for an ultrasonic e-cigarette device, according to some embodiments.

Referring to FIGS. 6-11B, in some embodiments, the ultrasonic e-cigarette device may be implemented through a different design, as shown. FIG. 6 shows an exploded view of an alternative implementation. In this case, the e-cigarette device includes a mouthpiece 602, a spray disk system encased in a spray disk housing 604 having a single spray disk, a liquid container 606, circuitry for actuating the spray disk 608, a battery container 610 and a battery cap 612, as shown.

Figure 7:
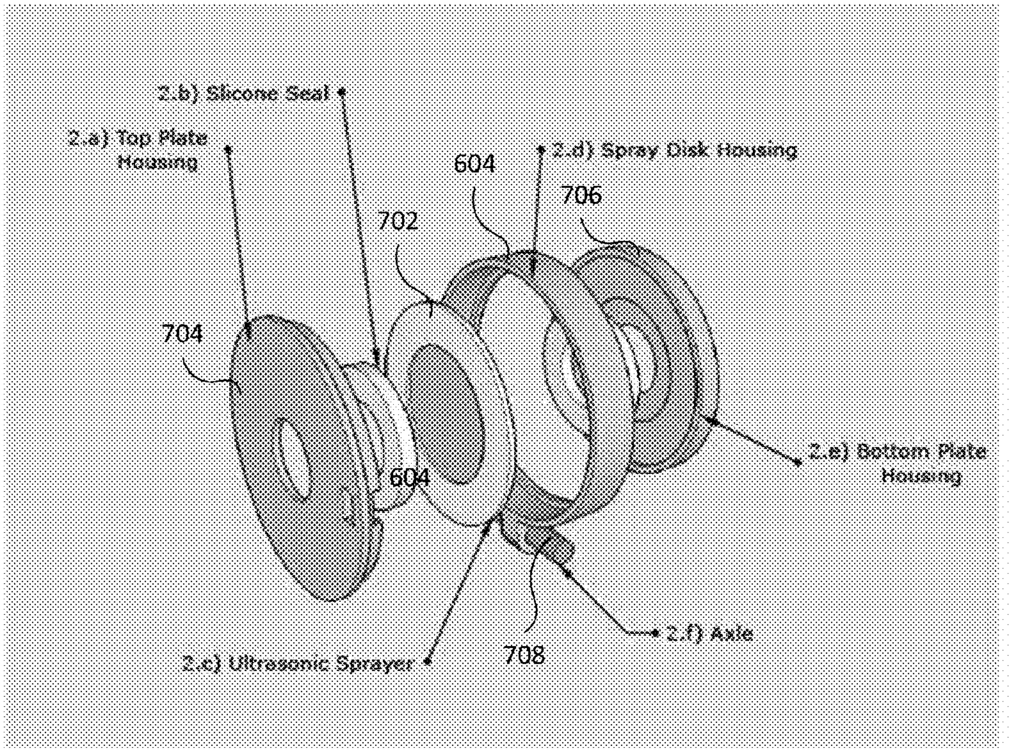
FIG. 7 shows an exploded view of the spray disk housing of the alternative design, according to some embodiments.
Figure 7:
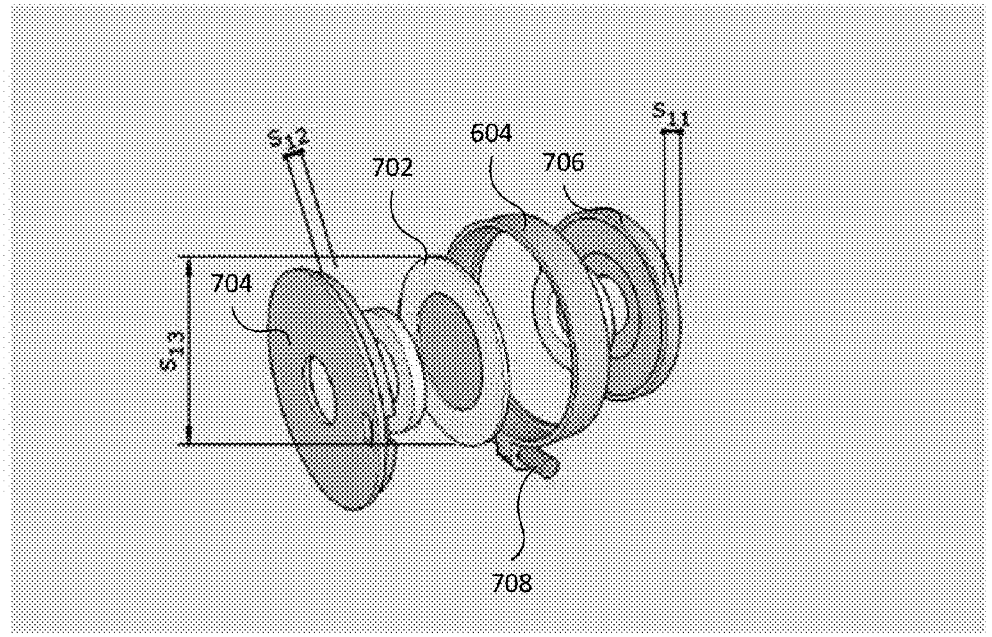

FIG. 7 shows an exploded view of the spray disk system of an alternative design, according to some embodiments. Here, the ultrasonic sprayer system includes a single disk 702, housed within a top plate housing 704 and a bottom plate housing 706 and including a seal and spray disk housing 604 with an axle to anchor the spray disk system to the mouthpiece and liquid container. Also shown are example dimensions of the spray disk system.

In this alternative example, various components may be similar to those described in FIGS. 1-5, however this time there is no water channel. Instead, the sprayer disk housing (see FIGS. 7-8C) sits directly above the liquid, and the sprayer is pushed down into the liquid container 606 when the cap 602 is screwed on. The sprayer and sprayer to liquid container interface may be airtight. This way, the stopper 902 (See FIG. 9A) located at the bottom of the liquid container 606 will move upwards as the liquid is used up.

Also, instead of using the stopper 902, one may employ a plastic bag or other flexible cartridge that has opening attachment which sits between the interface of the sprayer housing 604 and liquid container 606. The flexible cartridge may be configured to reduce in volume as the liquid in the cartridge is used up. This way, disposable cartridges may be utilized.

Figure 8A:
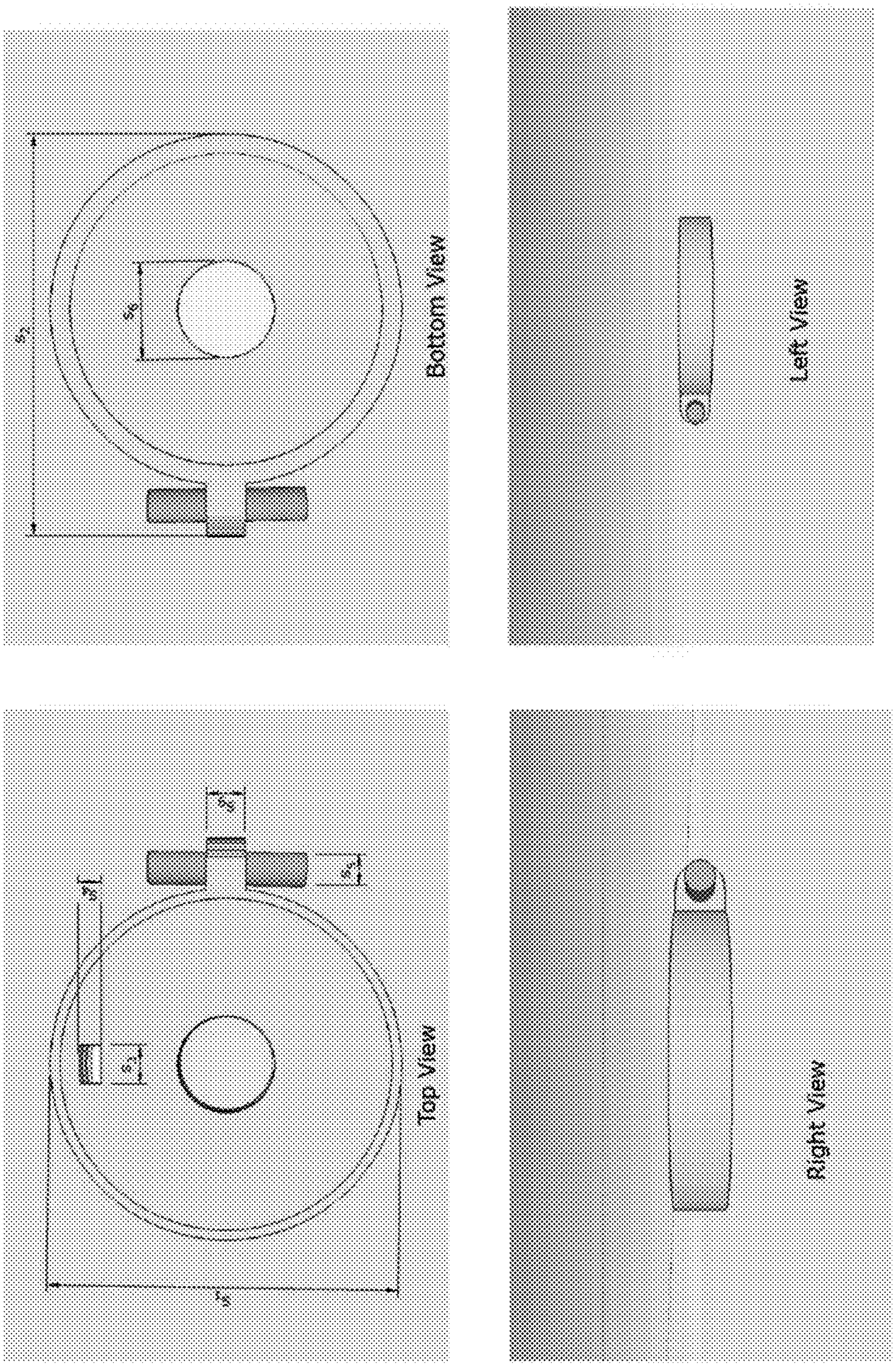
FIGS. 8A-8C show various angles of an assembled spray disk housing of the alternative design, according to some embodiments.
Figure 8B:
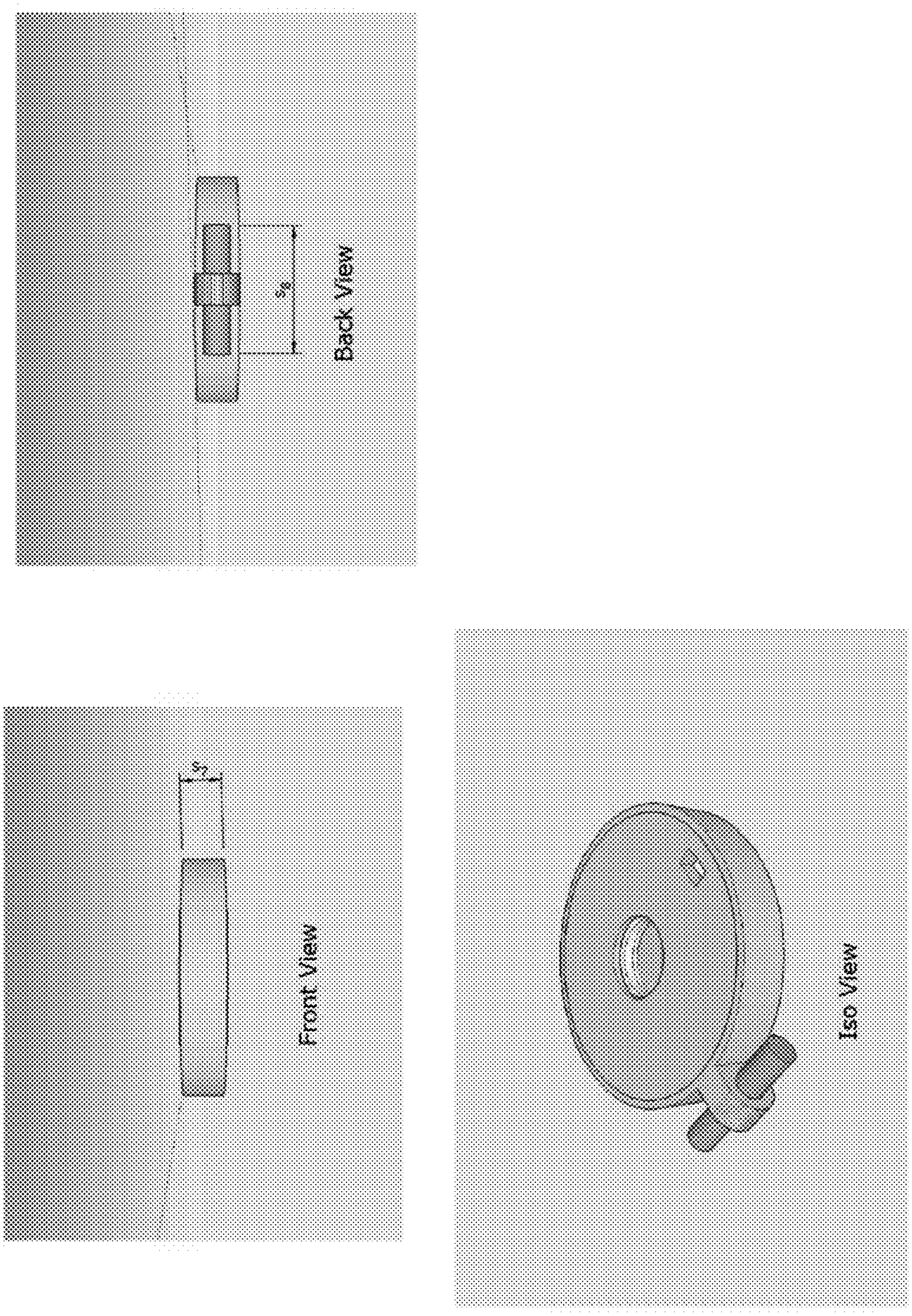
Figure 8C:
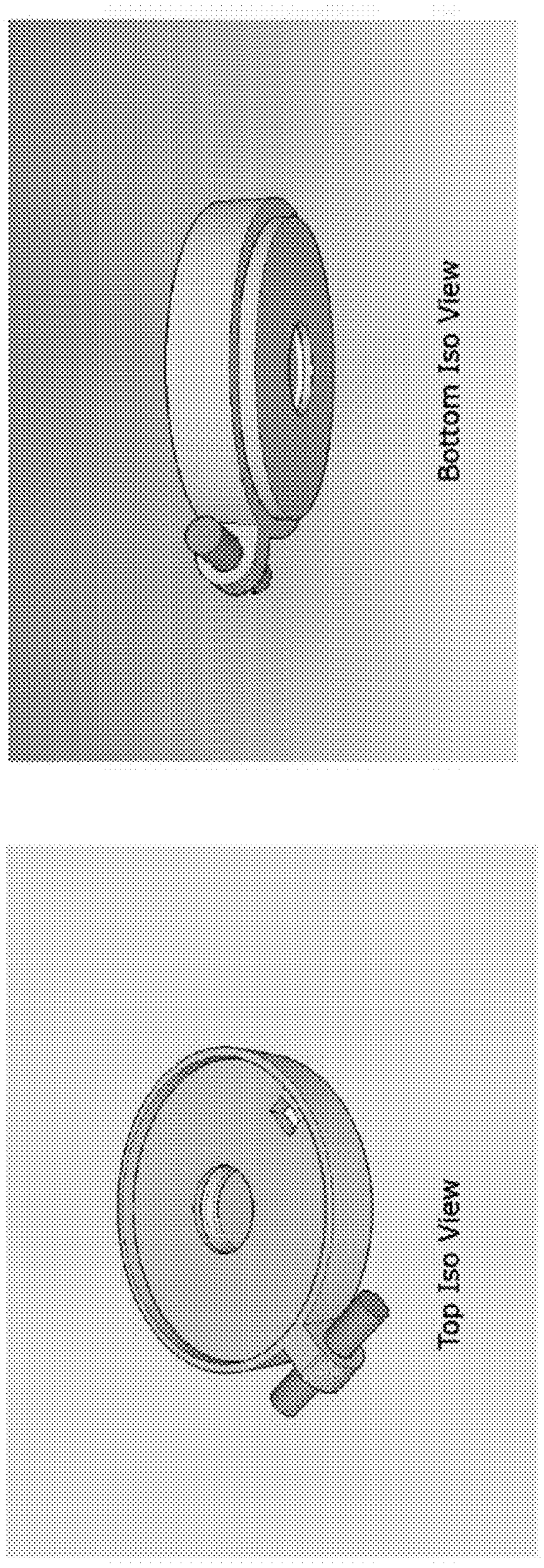

FIGS. 8A-8C show various views of the assembled spray disk housing 604 of an alternative design, according to some embodiments. FIG. 8A shows a top view, a bottom view, and views from the right and left of the spray disk housing when assembled. Example dimensions are illustrated as shown. FIG. 8B shows a front and back view of the spray disk housing, as well as an isometric view. It may be apparent that the spray disk is housed inside, with a hole in the middle of the housing to allow for the atomized liquid to spray through. FIG. 8C shows a top isometric view and a bottom isometric view of the spray disk housing.

Figure 9A:
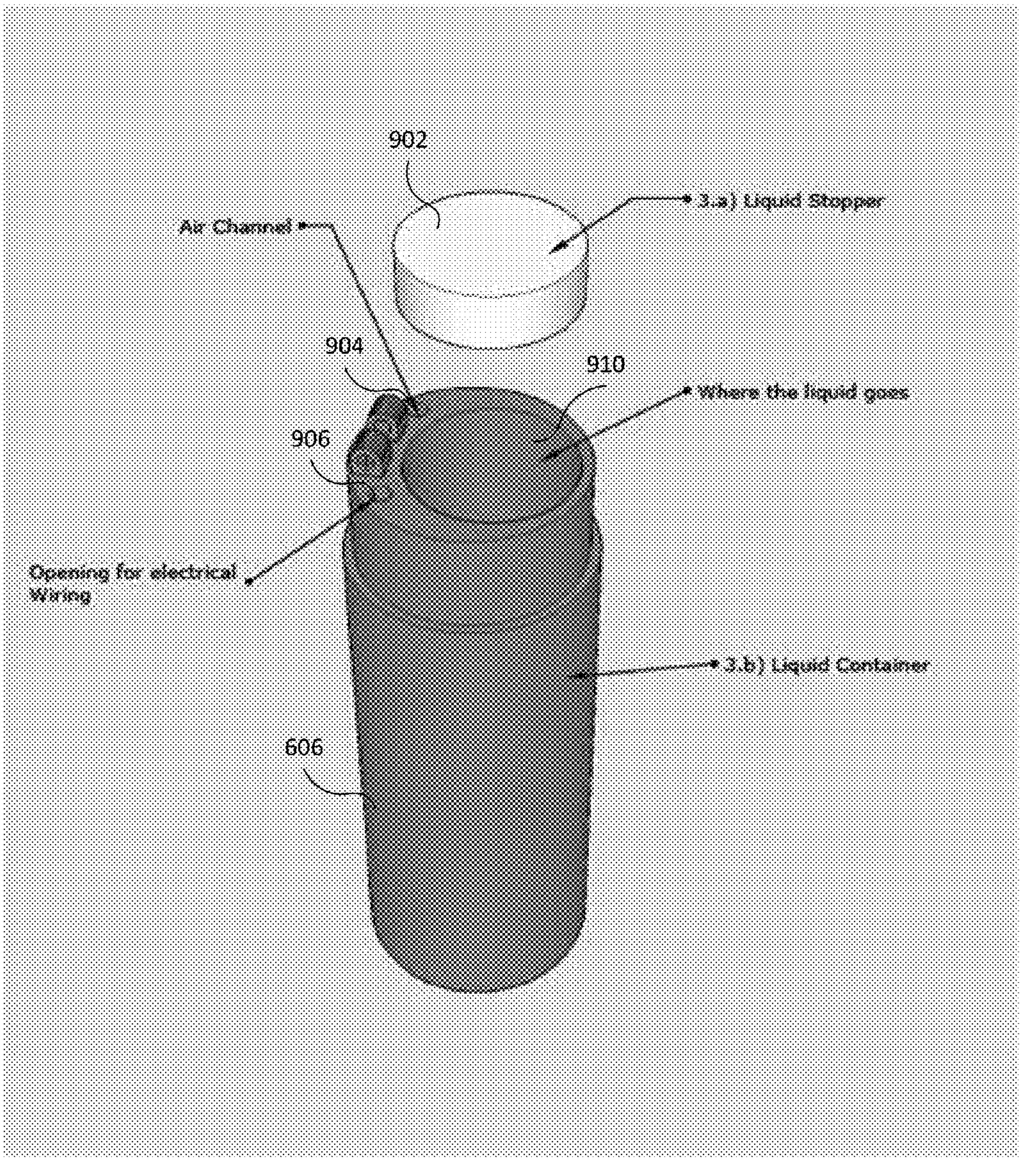
FIGS. 9A-9B show various angles of the liquid container system of the alternative design, according to some embodiments.
Figure 9B:
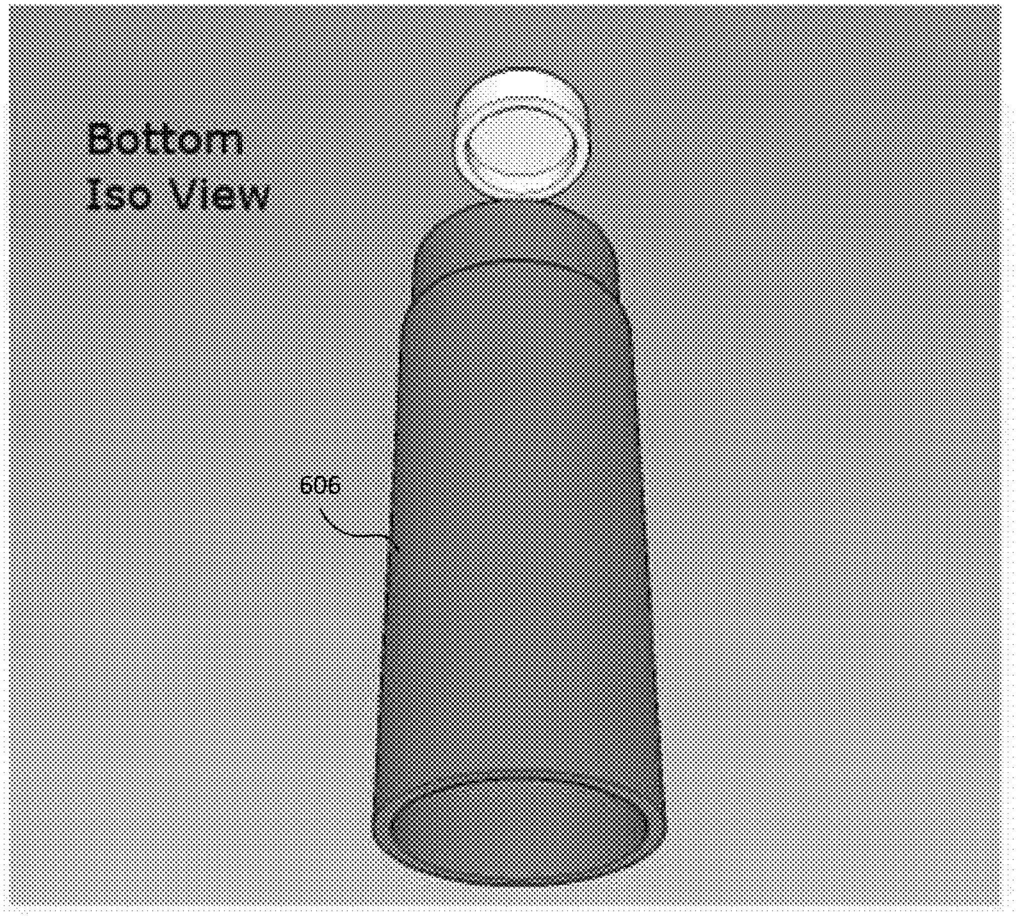

FIGS. 9A-9B show views of a liquid container of an alternative design, according to some embodiments. In FIG. 9A, the liquid container 606 includes a liquid stopper 902, an air channel 904, an opening 906 for electrical wiring to the circuitry below, and a larger opening 910 for where the liquid will be stored. FIG. 9B shows a bottom isometric view of the liquid container 606. As shown, the liquid container may store the liquid with the liquid stopper capping the liquid and raising or lowering as there is more or less liquid, respectively. In other cases, a flexible bag may contain cartridges of the liquid, where the top of the bag may attach between the spray disk housing and the top of the liquid container, not shown.

Figure 10:
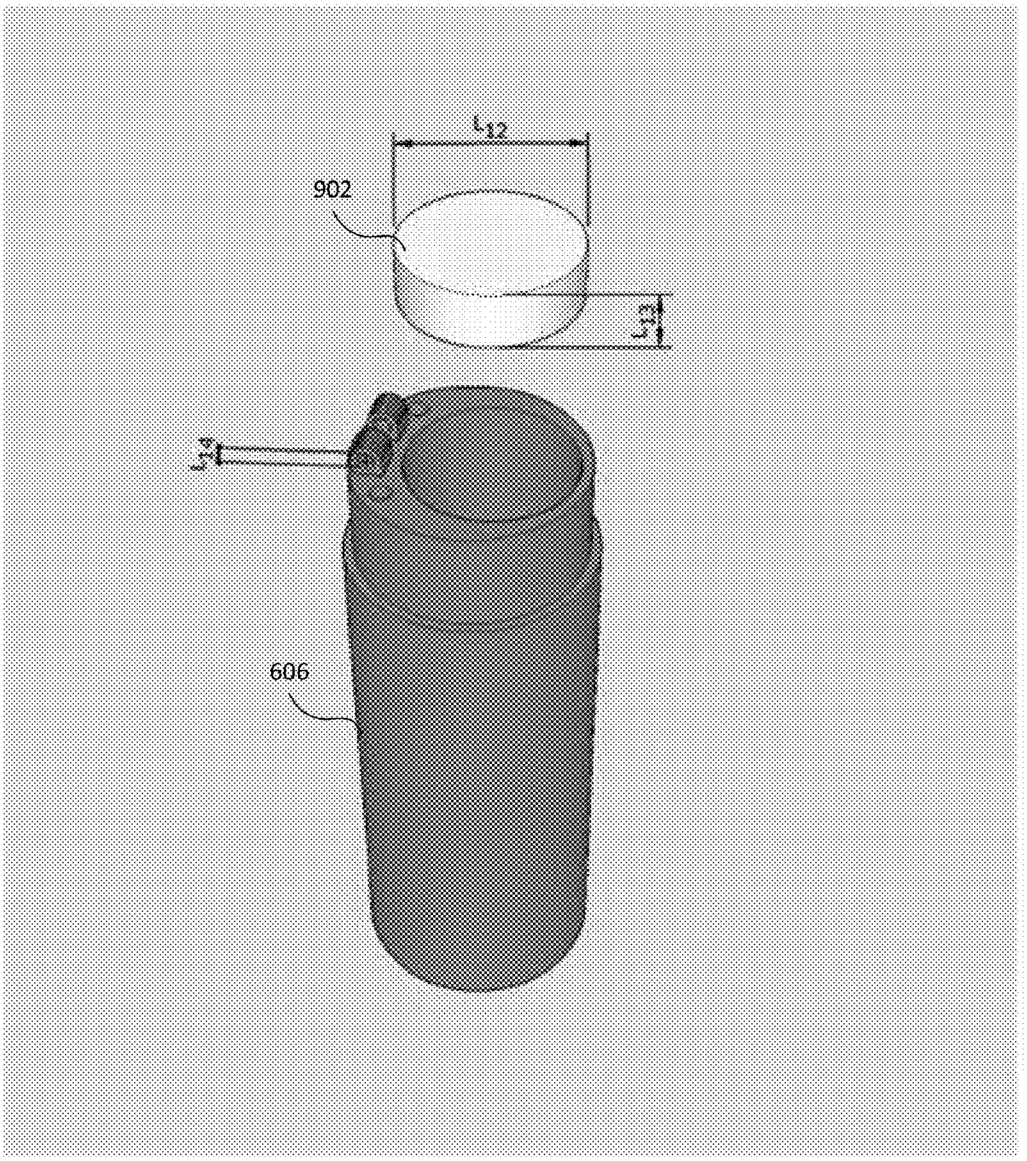
FIG. 10 shows various dimensions of the liquid container system, according to some embodiments.

FIG. 10 shows various dimensions of the liquid container 606 and the liquid stopper 902 that may be relevant to consider when implementing this design according to some embodiments.

Figure 11A:
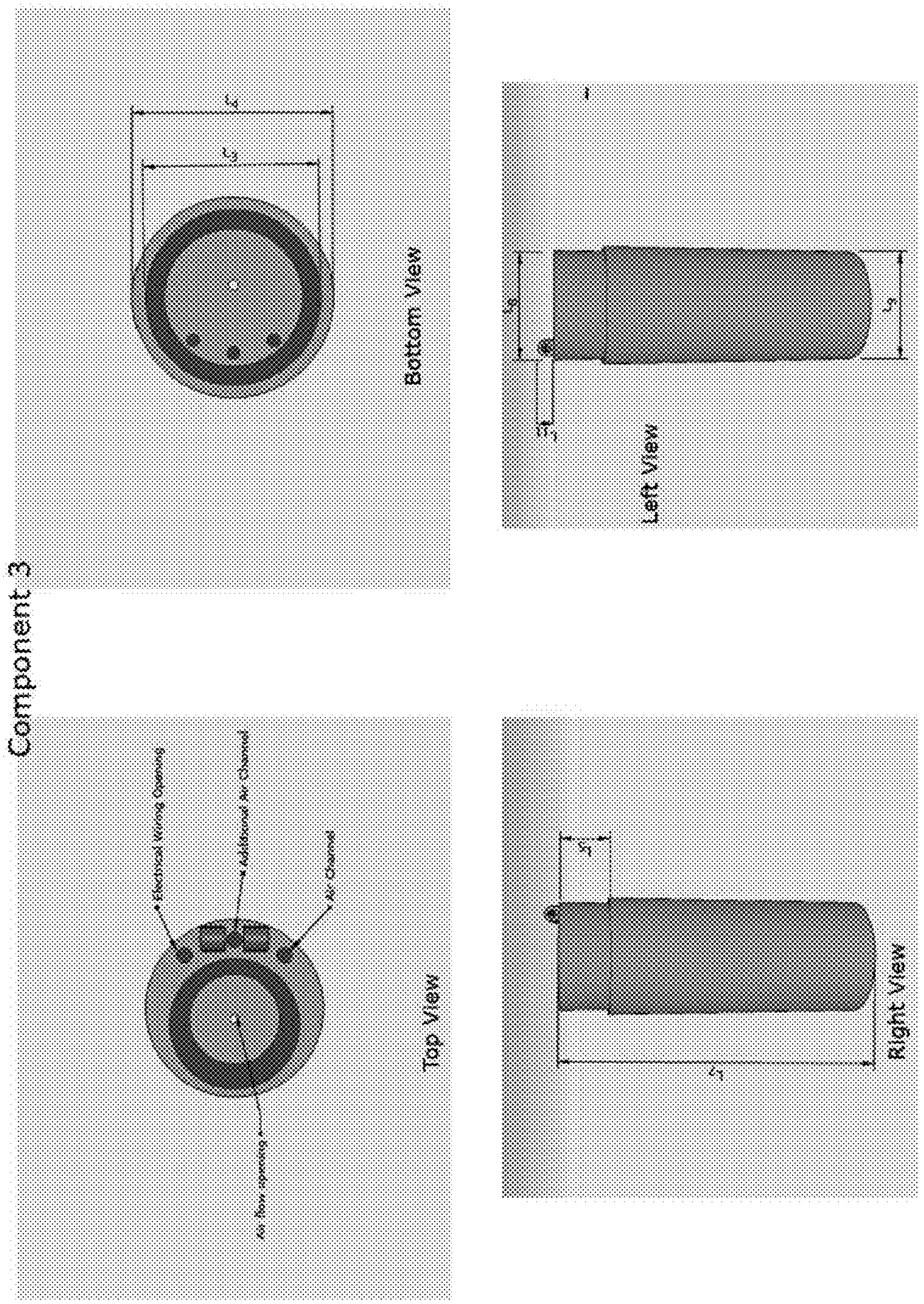
FIGS. 11A-11B show various angles of the liquid container, according to some embodiments.
Figure 11B:
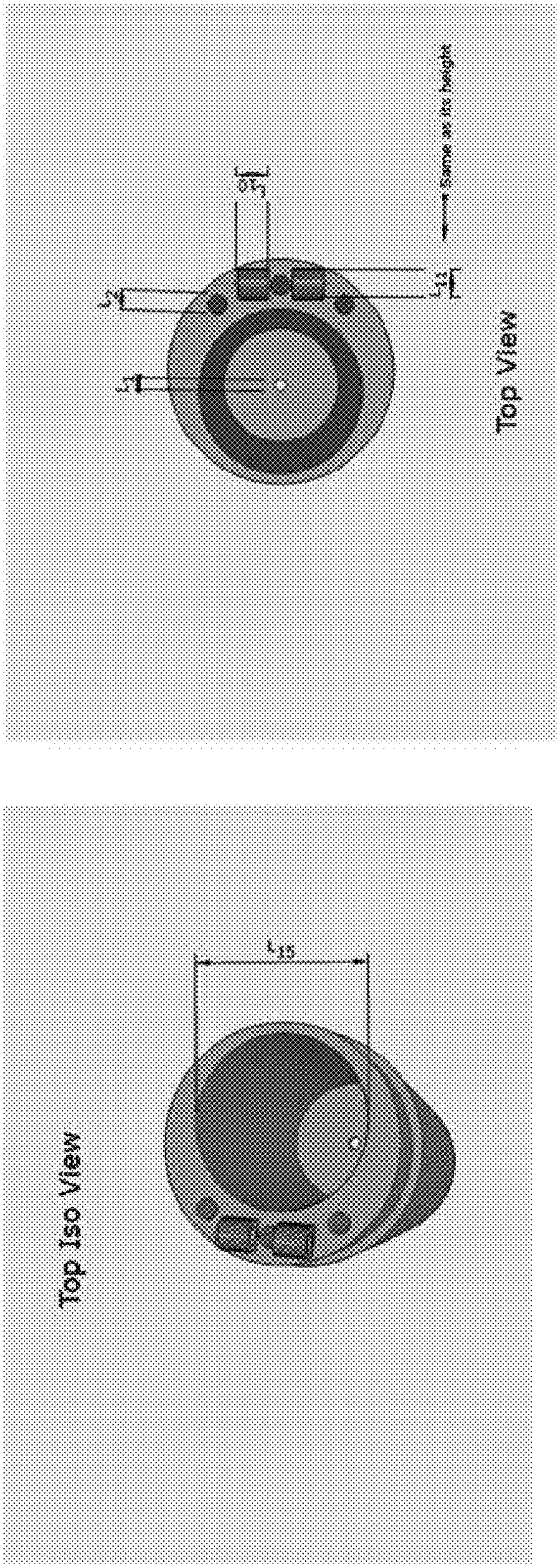

FIGS. 11A-11B show various angles of the liquid container, according to some embodiments. FIG. 11A shows a top view, a bottom view, and right and left views of the liquid container, including various dimensions that may be relevant for implementing this alternative design. FIG. 11B shows a top isometric view and a top view of the liquid container.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The present disclosure is illustrative and not limiting. Further modifications will be apparent to one skilled in the art in light of this disclosure and are intended to fall within the scope of the appended claims.

What is claimed is:

1. An apparatus for atomizing liquid into a breathable vapor, the apparatus comprising:

a liquid container housing comprising an inside volume and a bottom surface;

an inner liquid container housing positioned inside the liquid container such that liquid is configured to flow in between the inside volume of the liquid container housing and an outside volume of the inner liquid container housing, within a gap formed at a bottom end of the liquid container, and into an inside volume of the inner liquid container housing through the gap at the bottom end of the liquid container; and an ultrasonic liquid atomizer component positioned inside the inner liquid container and comprising:

an inner disk housing comprising a water channel and a liquid opening fluidically coupled to the water channel;

a first ultrasonic sprayer disk fluidically coupled to the liquid opening of the inner disk housing on a first side;

a second ultrasonic sprayer disk fluidically coupled to the liquid opening of the inner disk housing on a second side opposite the first side;

a first outer disk housing enclosing the first ultrasonic sprayer disk between the inner disk housing and the first outer disk housing and comprising a first air channel fluidically coupled to the first ultrasonic sprayer disk;

a second outer disk housing enclosing the second ultrasonic sprayer disk between the inner disk housing and the second outer disk housing and comprising a second air channel fluidically coupled to the second ultrasonic sprayer disk;

wherein the ultrasonic liquid atomizer is configured to vaporize liquid flowing within the inner liquid container directionally out through the first air channel and the second air channel by ultrasonically vibrating the first and second ultrasonic sprayer disks upon contact with the liquid.

2. The apparatus of claim 1, wherein the inner liquid container further comprises a third air channel positioned within the inside volume of the inner liquid container and outside of the ultrasonic liquid atomizer; wherein the third air channel is fluidically coupled to at least one of the first and second air channels and is physically isolated from the gap at the bottom of the liquid container by the positioning of the ultrasonic liquid atomizer.

3. The apparatus of claim 2, further comprising a cap enclosing the liquid container at a top end, and encapsulating the inner liquid container and the ultrasonic liquid atomizer within the liquid container.

4. The apparatus of claim 3, wherein the cap comprises an airway fluidically coupled to the third air channel of the inner liquid container configured to allow liquid vapor to flow out of the cap.

5. The apparatus of claim 4, wherein the cap further comprises a mouthpiece fluidically coupled to the airway and configured to allow suction of liquid vapor flowing out of the airway.

6. The apparatus of claim 1, further comprising an integrated circuit coupled to the bottom end of the liquid container and communicatively coupled to the ultrasonic liquid atomizer, the integrated circuit configured to cause the first and second ultrasonic sprayer disks to vibrate.

7. The apparatus of claim 6, further comprising a battery tube configured to contain a battery and encasing at least a portion of the integrated circuit.

8. The apparatus of claim 2, wherein:

the third air channel of the inner liquid container is fluidically coupled to the first air channel and not the second air channel;

the inner liquid container further comprises a fourth air channel positioned within the inside volume of the inner liquid container and outside of the ultrasonic liquid atomizer; and the fourth air channel is fluidically coupled to the second air channel and is physically isolated from the gap at the bottom of the liquid container by the positioning of the ultrasonic liquid atomizer.

9. The apparatus of claim 8, further comprising a cap enclosing the liquid container at a top end, and encapsulating the inner liquid container and the ultrasonic liquid atomizer within the liquid container, the cap comprising:

a first airway fluidically coupled to the third air channel of the inner liquid container and configured to allow liquid vapor to flow out of the cap; and a second airway fluidically coupled to the fourth air channel of the inner liquid container and configured to allow liquid vapor to flow out of the cap.

10. The apparatus of claim 1, wherein the ultrasonic liquid atomizer further comprises:

third and fourth ultrasonic sprayer disks fluidically coupled to the liquid opening of the inner disk housing on the first side; and fifth and sixth ultrasonic sprayer disks fluidically coupled to the liquid opening of the inner disk housing on the second side.

11. The apparatus of claim 10, wherein:

the first outer disk housing further encloses the third and fourth ultrasonic sprayer disks between the inner disk housing and the first outer disk housing and further comprises:

a third air channel fluidically coupled to the third ultrasonic sprayer disk; and a fourth air channel fluidically coupled to the fourth ultrasonic sprayer disk; and the second outer disk housing further encloses the fifth and sixth ultrasonic sprayer disks between the inner disk housing and the second outer disk housing and further comprises:

a fifth air channel fluidically coupled to the fifth ultrasonic sprayer disk; and a sixth air channel fluidically coupled to the sixth ultrasonic sprayer disk.

12. An apparatus for atomizing liquid into a breathable vapor, the apparatus comprising:

a liquid container housing comprising an inside volume, a bottom surface; and a hinge positioned on a top surface opposite the bottom surface and above the inside volume;

an ultrasonic liquid atomizer component positioned on the top surface and above the inside volume and rotatably coupled to the hinge, the ultrasonic liquid atomizer comprising:

an ultrasonic sprayer disk;

a spray disk housing;

a bottom plate housing comprising a liquid channel opening; and a top plate housing comprising an air channel opening, wherein:

the ultrasonic sprayer disk is encapsulated within an enclosure formed by coupling of the spray disk housing inbetween the bottom plate housing and the top plate housing;

the ultrasonic sprayer disk is fluidically coupled to the liquid channel opening of the bottom plate housing and the air channel opening of the top plate housing; and the ultrasonic liquid atomizer is configured to vaporize liquid flowing within the inside volume directionally out through the liquid channel opening and the air channel opening by ultrasonically vibrating the ultrasonic sprayer disk upon contact with the liquid.

13. The apparatus of claim 12, further comprising a liquid stopper and a cap.

14. The apparatus of claim 13, wherein the cap encloses the top surface of the liquid container and the liquid stopper is positioned within the inside volume of the liquid container.

15. The apparatus of claim 14, wherein an airtight seal is formed within the inside volume inbetween the cap and the liquid stopper by the enclosing of the top surface by the cap and the liquid stopper.

16. The apparatus of claim 15, wherein when liquid stored in the inside volume inbetween the liquid stopper and the ultrasonic liquid atomizer is vaporized directionally out through the liquid air channel, the liquid stopper is configured to rise up toward the ultrasonic sprayer disk due to a vacuum caused by the vaporization of the liquid and the airtight seal.

17. The apparatus of claim 12, further comprising an integrated circuit coupled to the bottom end of the liquid container and communicatively coupled to the ultrasonic liquid atomizer, the integrated circuit configured to cause the ultrasonic sprayer disk to vibrate.

18. The apparatus of claim 17, further comprising a battery tube configured to contain a battery and encasing at least a portion of the integrated circuit.

19. The apparatus of claim 12, further comprising a cap comprising an airway fluidically coupled to the air channel opening of the ultrasonic liquid atomizer and configured to allow liquid vapor to flow out of the cap.

20. The apparatus of claim 19, wherein the cap further comprises a mouthpiece fluidically coupled to the airway and configured to allow suction of liquid vapor flowing out of the airway.

* * * * *